United States Patent [19]

Rasberger et al.

[11] 4,185,006
[45] Jan. 22, 1980

[54] CYCLIC PHOSPHONITE STABILIZERS

[75] Inventors: Michael Rasberger, Riehen, Switzerland; John D. Spivack, Spring Valley, N.Y.

[73] Assignee: Ciba-Geigy Corporation, Ardsley, N.Y.

[21] Appl. No.: 922,394

[22] Filed: Jul. 6, 1978

[51] Int. Cl.² ............ C07F 9/48; C07F 9/65; C08K 5/53
[52] U.S. Cl. ............ 260/45.8 N; 260/45.7 P; 260/45.8 R; 260/45.8 SN; 260/45.85 T; 260/45.9 NC; 260/45.9 R; 260/45.95 G; 260/927 R
[58] Field of Search ............ 260/927 R (U.S. only), 260/928, 930 (U.S. only), 45.8 R

[56] References Cited

U.S. PATENT DOCUMENTS

| | | | |
|---|---|---|---|
| B 479,556 | 3/1976 | Luders et al. | 198/560 |
| 2,839,563 | 6/1958 | Hechenbleikner | 260/45.8 R |
| 3,205,252 | 9/1965 | Melton | 260/930 |
| 3,231,531 | 1/1966 | Buckley et al. | 260/45.75 W |
| 3,467,733 | 9/1969 | Dever et al. | 260/927 R |
| 3,488,407 | 1/1970 | Schall et al. | 260/927 R |
| 3,697,627 | 10/1972 | Rattenbury et al. | 260/928 |
| 3,702,878 | 11/1972 | Saito | 260/969 |
| 4,086,304 | 4/1978 | Hutton et al. | 260/927 R |

Primary Examiner—Howard E. Schain
Assistant Examiner—R. A. White
Attorney, Agent, or Firm—Vincent J. Cavalieri

[57] ABSTRACT

New phosphonites of the formula

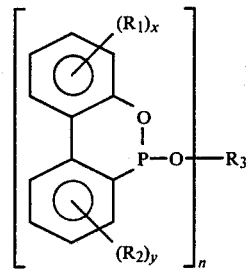

wherein
$R_1$ and $R_2$ independently of one another are a substituted or unsubstituted hydrocarbon radical, or halogen,
x and y independently of one another are 0, 1, 2 or 3,
n is 2, 3, 4, 5 or 6, and
$R_3$ is a n-valent substituted or unsubstituted aliphatic, alicyclic, aromatic, araliphatic or heterocyclic hydrocarbon residue as stabilizers for organic materials.

9 Claims, No Drawings

CYCLIC PHOSPHONITE STABILIZERS

The invention relates to new phosphonites, to the manufacture thereof, to their use as stabilisers for plastics and elastomers, and also to the polymers stabilised with these phosphonites.

Phosphonites are known stabilisers, especially 6-phenoxy-dibenz[c,e]-[1,2]-oxaphosphorine and 6-(2,6-di-tert.-butyl-4-methyl-phenoxy)-dibenz[c,e]-[1,2]-oxyphosphorine (Examples 9 and 10 of German Offenlegungsschrift No. 2,034,887). However, these phosphonites do not in every respect meet the high requirements which should be met by a stabiliser, particularly in respect of storage stability, absorption of water, sensitivity to hydrolysis, processing stabilisation, colour improvement, volatility, compatibility and improved stability to light.

It was the object of this invention therefore to provide stabilisers which do not have the disadvantages mentioned or have them to a lesser extent.

Accordingly, the invention relates to phosphonites of the formula I

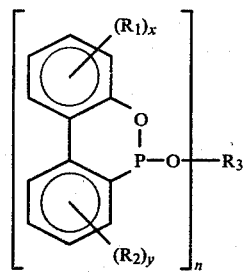

wherein
$R_1$ and $R_2$ independently of one another are a substituted or unsubstituted hydrocarbon radical, or halogen,
x and y independently of one another are 0, 1, 2 or 3,
n is 2, 3, 4, 5 or 6, and
$R_3$ is a n-valent substituted or unsubstituted aliphtic, alicyclic, aromatic, araliphatic or heterocyclic hydrocarbon residue.

Phosphonites of the formula I are in particular those wherein
$R_1$ is $C_1$-$C_8$ alkyl,
x is 0, 1 or 2 and
y is 0,
n is 2, 3, 4, 5 or 6 and
$R_3$, if n is 2, denotes $C_2$-$C_{22}$ alkylene which may optionally be interrupted by —O—, —S— or —N($R_4$)—, whereby $R_4$ is $C_1$-$C_{18}$ alkyl, $C_5$-$C_{12}$ cycloalkyl, $C_6$-$C_{14}$ aryl, benzyl or allyl, and $R_3$ denotes furthermore butenylene or butinylene, $C_5$-$C_{12}$ cycloalkylene, $C_6$-$C_{14}$ arylene, $C_7$-$C_{22}$ alkarylene, 1,4-dithian-2,5-diyl or a residue of the formula —$CH_2$—$CH_2$—$R_5$—, wherein $R_5$ is a member of the group consisting of

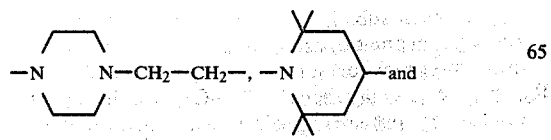

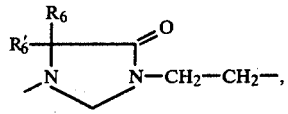

wherein $R_6$ and $R_6'$ denote independently of one another hydrogen or $C_1$-$C_6$ alkyl, and $R_3$ denotes furthermore a group of the formula

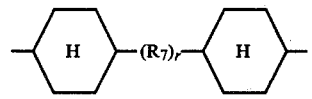

wherein r is 0 or 1 and $R_7$ denotes —O—, —S— or

whereby $R_8$ and $R_9$ denote independently of one another hydrogen or $C_1$-$C_8$ alkyl or $R_8$ and $R_9$ form together with the carbon atom to which they are attached a 5- to 12-membered ring, and $R_3$ denotes furthermore 1,4-cyclohexylenedimethylene; 1,3,3-trimethyl-cyclohexylene-1,5 or a group of the formula II

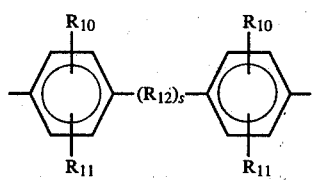

wherein s denotes 0 or 1, and
$R_{10}$ and $R_{11}$ denote independently of one another hydrogen, $C_1$-$C_{12}$ alkyl or cyclohexyl, and
$R_{12}$ denotes —O—, —S— or

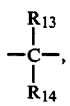

whereby
$R_{13}$ denotes hydrogen or $C_1$-$C_8$ alkyl and
$R_{14}$ denotes hydrogen, $C_1$-$C_8$ alkyl or one of the groups —$(CH_2)_a$—$COOR_{15}$ or —$CH_2$—$CH(R_{16})$—S—$R_{17}$, wherein a is 1 or 2, $R_{15}$ denotes $C_1$-$C_{18}$ alkyl, $C_5$-$C_8$ cycloalkyl, phenyl or benzyl and $R_{16}$ is hydrogen or methyl and $R_{17}$ denotes $C_1$-$C_{18}$ alkyl, cyclohexyl, phenyl, benzyl or a group —$(CH_2)_a$—$COOR_{15}$ wherein a and $R_{15}$ are as defined above, or $R_{13}$ and $R_{14}$ form together with the carbon atom to which they are attached a 5- to 12-membered ring and $R_3$ denotes furthermore a group of the formula III

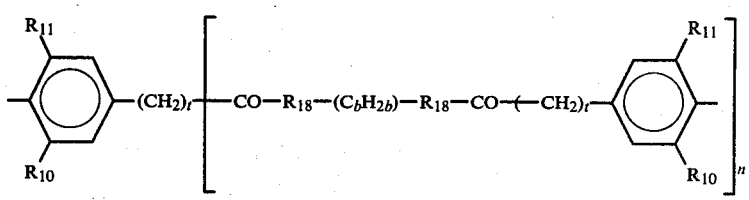

wherein
t is 0, 1, 2 or 3
$R_{18}$ is —O— or —NH—,
b is 1 to 18, and
$R_{10}$ and $R_{11}$ are as defined above, and
n is 0 or 1, and
$R_3$, if n is 3, denotes a trivalent aliphatic $C_3H_5$ to $C_7H_{13}$ hydrocarbon radical or one of the groups

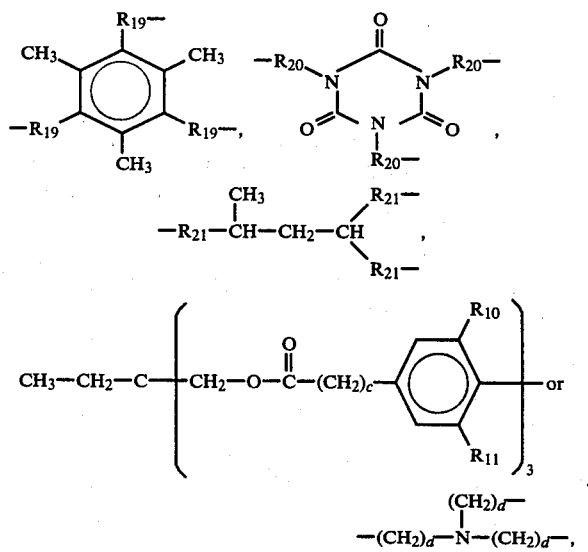

wherein d is 1 to 4 and
$R_{19}$ is a group of the formula IV

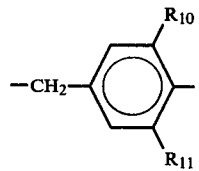

and $R_{10}$ and $R_{11}$ are as defined above, and
$R_{20}$ is a group of the formula IV wherein $R_{10}$ and $R_{11}$ are as defined above, or $R_{20}$ is —CH$_2$—CH$_2$— or a group of the formula V

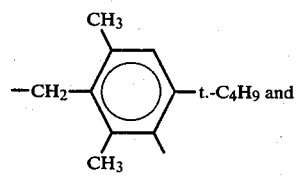

$R_{21}$ denotes a group of the formula VI

c is 0, 1, 2 or 3, and
$R_3$, if n is 4, denotes a tetravalent aliphatic $C_4H_6$ to $C_{10}H_{18}$ hydrocarbon radical or one of the groups VII or VIII

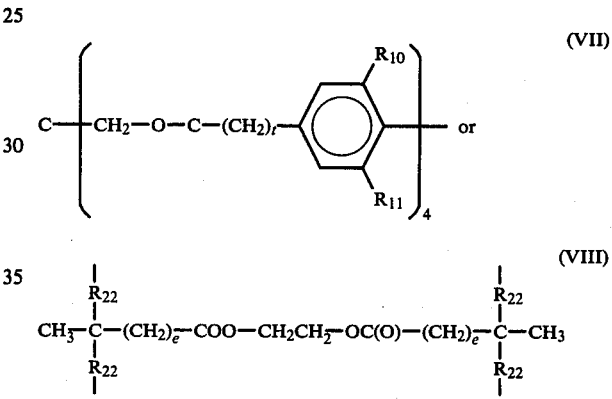

wherein $R_{22}$ is a group of the formula VI and e denotes 1 or 2, and t is as defined above, and
$R_3$, if n is 5, denotes a pentavalent aliphatic $C_5H_7$ to $C_{10}H_{17}$ hydrocarbon radical or the group IX

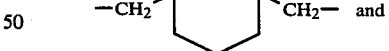

$R_3$, if n is 6, denotes a hexavalent aliphatic $C_6H_8$ to $C_{10}H_{16}$ hydrocarbon radical.

A substituted or unsubstituted hydrocarbon radical $R_1$ or $R_2$ is especially a radical of this type having 1–8 C atoms, such as straight-chain or branched-chain alkyl having 1–8 C atoms, for example methyl, i-propyl or tert.-butyl, and halogen $R_1$ or $R_2$ is particularly chlorine.

x is 1 or 2 and most preferably 0, y is preferably 0, and n is 2, 3, 4, 5 or 6, preferably 2, 3 or 4 and most preferably 2 or 3.

$R_3$ is a n-valent substituted or unsubstituted aliphatic, alicyclic, aromatic, araliphatic or heterocyclic hydrocarbon residue.

$R_3$, if n is 2, may be $C_2$–$C_{22}$ alkylene, preferred $C_2$–$C_9$ and most preferred $C_2$–$C_6$ alkylene such as dimethylene, trimethylene, tetramethylene, hexamethylene, octamethylene, nonamethylene, 2,2,4-trimethylhexamethylene, decamethylene, dodecamethylene, octadecamethylene or docosamethylene. The alkylene group may be interrupted by —O—, —S— or —N($R_4$)— such as in 2-thiapropylene-1,3; 3-thiapentylene-1,5; 4-oxaheptamethylene, 3,6-dioxaoctylmethylene-1,8 or 3,6-diazaoctylene-1,8. The nitrogen of the aza-group may be substituted by $R_4$ denoting e.g. $C_1$–$C_{18}$ alkyl, such as methyl, ethyl, n-propyl, iso-propyl, n-butyl, sec.-butyl, t.-butyl, n-pentyl, n-hexyl, iso-hexyl, n-octyl, 1,1,3,3-tetramethylbutyl, n-nonyl, decyl, dodecyl, tetradecyl, hexadecyl or octadecyl.

As $C_5$–$C_{12}$ cycloalkyl $R_4$ is e.g. cyclopentyl, cyclohexyl, cycloheptyl, cyclooctyl or cyclododecyl. As $C_6$–$C_{10}$ aryl $R_4$ is e.g. phenyl or naphthyl.

Examples for $R_3$ $C_5$–$C_{12}$ cycloalkylene are 1,2-cyclopentylene, 1,3-cyclohexylene, 1,4-cyclohexylene, 1,4-cycloheptylene or 1,2-cyclononylene. $C_6$–$C_{10}$ arylene as $R_4$ means e.g. 1,4-phenylene or 1,5-naphthylene, preferably 1,4-phenylene.

$R_3$ may be $C_7$–$C_{22}$ alkarylene, and is preferably a phenylene-1,4-group, which is mono- or dialkylated particularly in 2-, 2,5- or 2,6-position. In most preferred compounds the alkyl-groups in 2- and 5- or 6-position are identical.

Examples of $C_7$–$C_{22}$ alkarylene groups as $R_3$ are 2,5-di.-t.-butylphenylene-1,4; 2,5-di-t.-pentylphenylene-1,4; 2,5-di-t.-octylphenylene-1,4; 2-t.-butyl-5-methylphenylene-1,4; 2,6-di-t.-butylphenylene, 2,5-diisopropylphenylene-1,4; 2-t.-butylphenylene-1,4; or 2-t.-octylphenylene-1,4.

The groups $R_6$ and $R_6'$ are preferably hydrogen or alkyl groups with 1 to 6 carbon atoms, such as methyl, ethyl, n-propyl, n-butyl or n-hexyl.

$R_8$, $R_9$, $R_{13}$ and $R_{14}$ are in particular $C_1$–$C_8$-alkyl such as methyl, ethyl, n-propyl, n-butyl, n-hexyl or n-octyl. The preferred meaning of $R_8$, $R_9$, $R_{13}$ and $R_{14}$ are hydrogen, methyl, ethyl or n-propyl. Most preferably $R_8$, $R_9$, $R_{13}$ and $R_{14}$ denote hydrogen or methyl.

Furthermore, $R_8$ and $R_9$ or $R_{13}$ and $R_{14}$ form together with the carbon atom to which they are attached a 5- to 12-membered ring, such as a cyclopentyl-, cyclohexyl-, cycloheptyl-, cyclooctyl- or cyclododecyl-ring.

$R_{10}$ and $R_{11}$ are preferably in ortho-position to the free valence and may be $C_1$–$C_{12}$ alkyl, such as methyl, ethyl, isopropyl, sec.-butyl, t.-butyl, t.-pentyl, n-hexyl, 2-ethylhexyl, 1,1,3,3-tetramethylbutyl, n-decyl or 1,1,3,3,5,5-hexamethylhexyl, preferred are $C_1$–$C_8$ alkyl groups.

$R_{15}$ and $R_{17}$ may be $C_1$–$C_{18}$ straight chain or branched alkyl, such as methyl, ethyl, n-propyl, n-butyl, n-hexyl, 2-ethyl-hexyl, n-decyl, n-dodecyl, n-tetradecyl or n-octadecyl.

As $C_5$–$C_8$ cycloalkyl $R_{15}$ may be cyclopentyl, cyclohexyl, cycloheptyl or cyclooctyl, preferably cyclohexyl.

$R_{18}$ denotes —NH— and particularly —O—, b may be 1 to 18, preferably 2 to 6.

$R_3$, if n is 3, may be trivalent aliphatic $C_3H_5$ to $C_7H_{13}$ hydrocarbon radical, such as

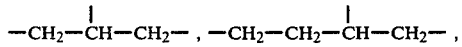

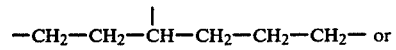

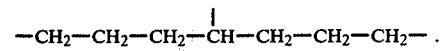

$R_4$, if n is 4, may be a tetravalent aliphatic $C_4H_6$ to $C_{10}H_{18}$ hydrocarbon radical, such as

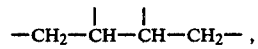

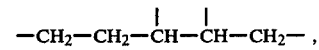

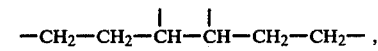

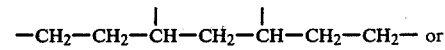

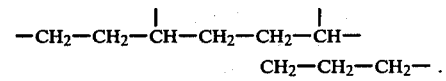

$R_5$, if n is 5, may be a pentavalent aliphatic $C_5H_7$ to $C_{10}H_{17}$ hydrocarbon radical, such as

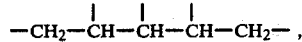

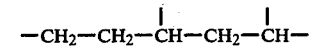

$R_6$, if n is 5, is a hexavalent aliphatic $C_6H_8$ to $C_{10}H_{16}$ hydrocarbon radical, such as

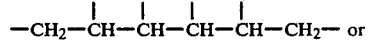

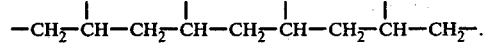

Preferred phosphonites of the formula I are those wherein x and y are 0, and n is 2, 3 or 4, and $R_3$, if n is 2, denotes $C_2$–$C_9$ alkylene which may optionally by interrupted by —O— or —S—, or $R_3$ denotes furthermore phenylene, or phenylene which is mono- or di-alkylated with a total number of carbon atoms of 7–22 or a group of the formula II*,

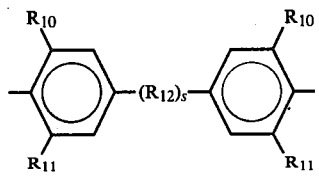 (II*)

wherein
denotes 0 or 1, and
$R_{10}$ and $R_{11}$ denote independently of one another hydrogen or $C_1$-$C_8$ alkyl and $R_{12}$ denotes —O—, —S— or

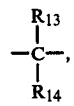

whereby
$R_{13}$ is hydrogen or methyl, and
$R_{14}$ is hydrogen, methyl or one of the groups —(CH$_2$)$_a$— COOR$_{15}$ or —CH$_2$—CH(R$_{16}$)—S—R$_{17}$ wherein a and $R_{16}$ are as defined above and $R_{15}$ denotes $C_1$-$C_{18}$ alkyl and $R_{17}$ is $C_1$-$C_{12}$ alkyl or a group of the formula —(CH$_2$)$_a$—COOR$_{15}$, wherein a and $R_{15}$ are as herein defined and $R_3$ denotes furthermore a group of the formula III wherein $R_{10}$ denotes methyl or t.butyl, and $R_{11}$ is t.butyl, $R_{18}$ is —O— or —NH—, t is 2, b is 2 to 6 and n is 1, and
$R_3$, if n is 3, denotes a trivalent aliphatic $C_3H_5$ to $C_7H_{13}$ hydrocarbon radical or a group of the formula

—R$_{21}$—CH(CH$_3$)—CH$_2$—CH(R$_{21}$—)(R$_{21}$—), wherein
$R_{21}$ is as defined above, and
$R_3$, if n is 4, denotes a group of the formula VII, wherein t is 2 and $R_{10}$ and $R_{11}$ denote t.butyl.

Most preferred phosphonites of the formula I are those wherein
x and y are 0, and
n is 2 or 3, and
$R_3$, if n is 2, denotes $C_2$-$C_6$ alkylene, which may be optionally interrupted by —O— or —S—, or $R_3$ denotes phenylene or phenylene, which is mono- or di-alkylated with a total number of carbon atoms of 7-22, or a group of the formula II*, wherein s denotes 0 or 1, and $R_{10}$ and $R_{11}$ denote independently of one another hydrogen, methyl, t.butyl, t.pentyl or 1,1,3,3-tetramethylbutyl and $R_{12}$ is —O—, —S— or

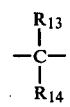

wherein
$R_{13}$ and $R_{14}$ are hydrogen or methyl, and $R_3$ denotes furthermore a group of the formula III where-
$R_{10}$ denotes methyl or t.butyl and $R_{11}$ denotes t.butyl,
$R_{18}$ is —O—, t is 2, b is 2 to 6 and n is 1, and
$R_3$, if n is 3, denotes

—CH$_2$—CH(|)—CH$_2$— or a group of the formula

—R$_{21}$—CH(CH$_3$)—CH$_2$—CH(R$_{21}$—)(R$_{21}$—), $R_{21}$ is as defined above.
Examples of compounds of the formula I are:

1) Q—CH$_2$—CH$_2$—Q
2) Q'—(CH$_2$)$_{12}$—Q'
3) Q—CH$_2$—CH=CH—CH$_2$—Q
4) Q—CH$_2$—C≡C—CH$_2$—Q
5) Q"—CH$_2$—CH$_2$—O—CH$_2$—CH$_2$—O—CH$_2$—CH$_2$—Q"
6) Q—(cyclododecylene-1,2)—Q
7) Q—(1,4-dithian-diyl-2,5)—Q
8) 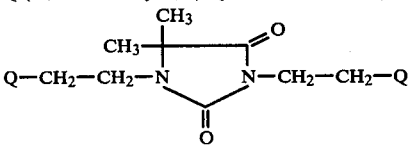
9) 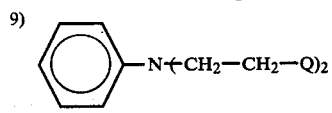
10) 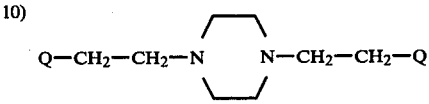
11) 
12) 
13) 
14) (Q''')$_{\overline{2}}$CH$_2$ -continued 15) 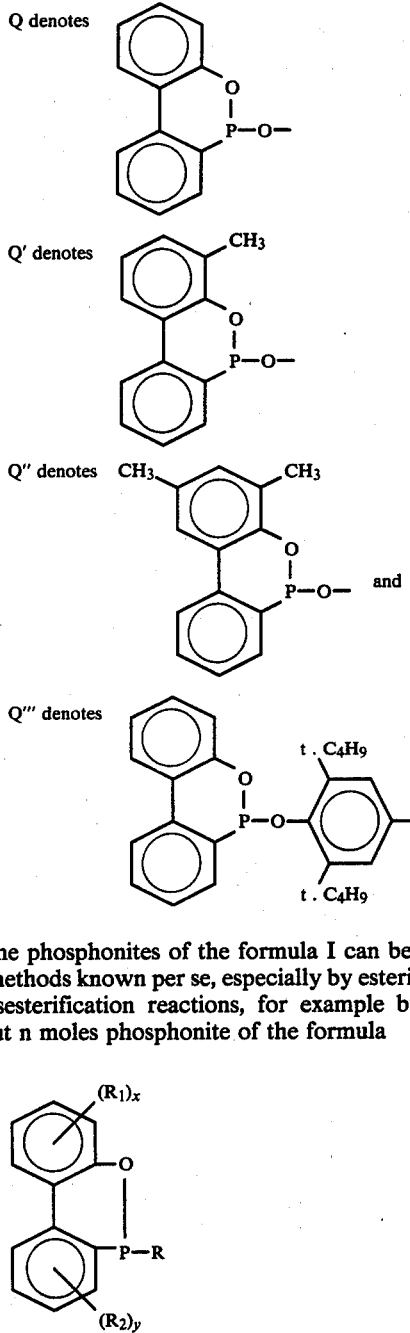

16)

17)

18) [Q'''—CH$_2$—CH$_2$COO—(CH$_2$)$_3$]$_2$
19) N(CH$_2$—CH$_2$—Q)$_3$
20) CH$_3$—CH$_2$—C(CH$_2$—Q)$_3$
21) Q—CH$_2$—CH(Q)—CH$_2$—Q

22)

23)

24)

25)

26) C(CH$_2$—Q)$_4$
27) Q—CH$_2$—CH(Q)—CH(Q)—CH$_2$—Q
28) [Q'''—CH$_2$—CH$_2$—COO—CH$_2$]$_4$C
29)

30) Q—CH$_2$—CH(Q)—CH(Q)—CH(Q)—CH$_2$Q
31) 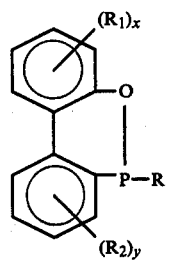

32) Q—CH$_2$—CH(Q)—CH(Q)—CH(Q)—CH(Q)—CH$_2$Q
33) (Q—CH$_2$)$_3$C—CH$_2$—O—CH$_2$—C(CH$_2$—Q)$_3$

In the formula 1 to 33 above

Q denotes

Q' denotes

Q'' denotes  and

Q''' denotes

The phosphonites of the formula I can be produced by methods known per se, especially by esterification or transesterification reactions, for example by reacting about n moles phosphonite of the formula

wherein R is a reactive group and R$_1$, R$_2$, x and y have the meanings defined in the fore going, with a polyol of the formula R$_3$(OH)$_n$ wherein R$_3$ and n have the meanings defined above.

A reactive group R is for example halogen, especially chlorine; alkoxy or substituted or unsubstituted phenoxy.

The reaction can be performed in a manner known per se, for example by heating, preferably to above about 80° C., in particular above 150° C., such as 150°–240° C., for example 220° C., in the course of which H R is split off, wherein R has the meaning defined above; or instead in the presence of bases, such as amines, for example triethylamine, pyridine, N,N-dimethylaniline or sodium carbonate, preferably in an inert solvent, such as aprotic solvents, for example ligroin, toluene, dimethylformamide, dimethylacetamide, sulpholane, methyl ethyl ketone, acetonitrile or ethyl acetate; and also amine bases in excess can be used and these can at the same time serve as solvents (see also German Offenlegungsschrift No. 2,034,887).

The starting materials are known and can, if they are novel, be produced by methods analogous to known methods. P—Cl phosphonites are known, for example, from German Offenlegungsschrift No. 2,034,887, whilst the starting phenols are compounds which have been known for a long time and which are in many cases available commercially.

The compounds of the formula I can be used according to the present invention as stabilisers for plastics and elastomers to protect these from damage caused by the action of oxygen, light and heat. Examples of plastics concerned are the polymers listed in the German Offenlegungsschrift No. 2,456,864 on pages 12–14.

Suitable substrates are, for example:

1. Polymers which are derived from mono-unsaturated hydrocarbons, such as polyolefins, for example low density and high density polyethylene, which can be crosslinked, polypropylene, polyisobutylene, polymethylbut-1-ene and polymethylpent-1-ene.
2. Mixtures of the homopolymers mentioned under 1, for example mixtures of polypropylene and polyethylene, of polypropylene and polybut-1-ene and of polypropylene and polyisobutylene.
3. Copolymers of the monomers on which the homopolymers mentioned under 1 are based, such as ethylene/propylene copolymers, propylene/but-1-ene copolymers, propylene/isobutylene copolymers and ethylene/but-1-ene copolymers, and also terpolymers of ethylene and propylene with a diene, for example hexadiene, di-cyclopentadiene or ethylidenenorbornene.
4. Polystyrene and its copolymers, such as SAN, ABS, IPS, ASA, and EP-modified styrene copolymers.
5. Polyamides.
6. Linear polyesters.
7. Polyurethanes.
8. Polycarbonates.
9. Elastomers, such as polybutadiene, SBR, polyisoprene, polychloroprene and nitrile rubber.
10. Thermoplastic elastomers, such as SBS, SIS and S-EP-S.
11. Polyvinyl chloride and the like.
12. Lubricating oils having a synthetic or mineral base.

The present invention relates also to a process for stabilising polymers against thermooxidative degradation during production, isolation, processing and use, which process comprises incorporating into the polymer at least one compound of the formula I/II.

The compounds of the formula I are incorporated into the substrates at a concentration of 0.005 to 5 percent by weight, calculated relative to the material to be stabilised.

Preferably 0.01 to 1.0 percent by weight, and particularly preferably 0.02 to 0.5 percent by weight, of the compounds, relative to the material to be stabilised, is incorporated into this material. Incorporation is effected for example by mixing at least one of the compounds of the formula I, and optionally further additives, by methods customary in the art, into the polymer either before or during shaping, or alternatively by application of the dissolved or dispersed compounds to the polymers, optionally with subsequent removal of the solvent by evaporation.

The new compounds can also be added in the form of a masterbatch, which contains these compounds for example at a concentration of 2.5 to 25 percent by weight, to the plastics to be stabilised.

In the case of crosslinked polyethylene, the compounds are added before crosslinking.

The invention relates therefore also to the plastics which are stabilised by the addition of 0.01 to 5 percent by weight of a compound of the formula I, and which can optionally contain further additives. The plastics stabilised in this way can be used in the widest variety of forms, for example as films, fibres, tapes and profiles, or as binders for lacquers, adhesives or putties.

Examples of further additives which can be used together with the stabilisers according to the invention are: antioxidants, UV absorbers and light stabilisers, such as 2-(2'-hydroxyhenyl)-benztriazoles, 2,4-bis-(2'-hydroxyphenyl)-6-alkyl-s-triazines, 2-hydroxybenzophenones, 1,3-bis-(2'-hydroxybenzoyl)benzenes, esters of substituted or unsubstituted benzoic acids and acrylates, and also nickel compounds, sterically hindered amines, oxalic acid diamides, metal deactivators, phosphites, compounds which destroy peroxide, polyamide stabilisers, basic Co stabilisers, nucleating agents or other additives, for example plasticisers, lubricants, emulsifiers, fillers, carbon black, asbestos, kaolin, talc, glass fibres, pigments, optical brighteners, flameproofing agents and antistatic agents.

The invention is further illustrated by the following Examples.

EXAMPLES 1–8

22,2 g (0,1 mole) of 2,5-di-t.butyl-hydroquinone and 46,8 g (0,2 moles) of 6-chloro-dibenz[c,e]-[1,2]oxaphosphorine are reacted for 3 hours at a temperature of 200° C. After the reaction has ended, the reaction mixture is held for further two hours at a temperature of 200° C. and cooled afterwards. The resulting

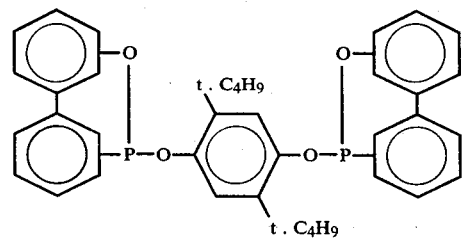

(Stabilizer 1).

melts at 258° C.

The following compounds are obtained analogously:

2) 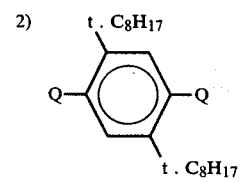  m.p. 190° C.

-continued

3) [structure with t.C4H9, CH2 bridge] m.p. 222° C.

4) [structure with t.C4H9, C(CH3)2 bridge] resin: P_calc: 8,41; P_found: 8,2

5) [structure with t.C4H9, C(CH3)(CH2-COOC2H5) bridge] resin: P_calc: 7,6; P_found: 6,9

6) Q—CH2—C(CH3)2—CH2—Q    oil: P_calc: 12,38; P_found: 12,4

7) Q—CH2—CH2—S—CH2—CH2—Q    oil: P_calc: 6,18; P_found: 6,71

8) Q—(CH2)6—Q    oil: C_calc: 70,03; C_found: 70,25

In Examples 2 to 8 Q denotes a residue of the formula

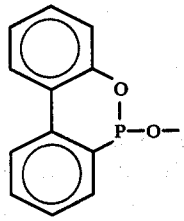

EXAMPLE 9

100 parts of polypropylene powder are mixed together with compound 1 and with pentaerythritol-tetra-kis-[3-(3,5-di-tert.-butyl-4-hydroxyphenyl)-propionate]. (Antioxidans A) in the amounts given in the following Table.

The resulting mixtures are extruded 5 times successively in a single screw extruder at a maximum of 260° C. with a speed of 100 rpm. The melt index of the polymer is measured after the 1st, 3rd and 5th extrusion, and for this purpose the load is 2160 g, the temperature 230° C. and the melt index is expressed in grams per 10 minutes. The degradation of the polymer is indicated by a rise in the melt index.

| parts | Stabilizer Nr. | Melt index after extrusion 1. | 3. | 5. |
|---|---|---|---|---|
|  | none | 14 | 42 | 76 |
| 0,15 | Antioxidans A | 4,8 | 6,5 | 9,0 |
| 0,1 | 1 | 2,6 | 4,6 | 6,8 |
| 0,05 | Antioxidans A |  |  |  |
| 0,05 | 1 | 2,5 | 3,7 | 5,0 |
| 0,05 | Antioxidans A |  |  |  |
| 0,1 | 1 | 2,5 | 3,5 | 4,8 |

EXAMPLE 10

100 parts of unstabilised polyethylene of high density having a molecular weight of about 500,000 ("Lupolen 5260 Z" in powder form from BASF) are in each case mixed dry with 0.05 part of pentaerythritol-tetra-[3-(3,5-di-tert.-butyl-4-hydroxyphenyl)propionate] and 0.1 part of the stabilizer of the following Table. The mixtures are kneaded in a Brabender plastograph at 220° C. and at 50 r.p.m. for 20 minutes. During this time, the resistance to kneading is continuously recorded as a torsional moment. Owing to cross-linking of the polymer, there occurs during the kneading period, after an initial constant stage, a rapid increase of the torsional moment. The effectiveness of the stabilizers is reflected in a lengthening of the time of constant torsional moment.

In an additional test the yellowness of the material is measured after 20 minutes kneading in the Brabender plastograph as described above. To assess the degree of yellowing, the Yellowness Index (Y.I.) according to ASTM D-1925/6-3T is measured. An increase of the value of the Y.I. denotes successively more severe discoloration of the material.

| Stabilizer Nr. | Time in minutes until change of torsional moment | Y.I. = Discoloration assessment of the test speciment |
|---|---|---|
| None | 1,5 | 8,2 |
| 1 | 16 | 8,8 |
| 2 | 12,5 | 4,1 |
| 3 | 16 | 2,4 |
| 5 | 12 | 2,5 |
| 6 | 4 | −1,9 |

What we claim is
1. New phosphonites of the formula I

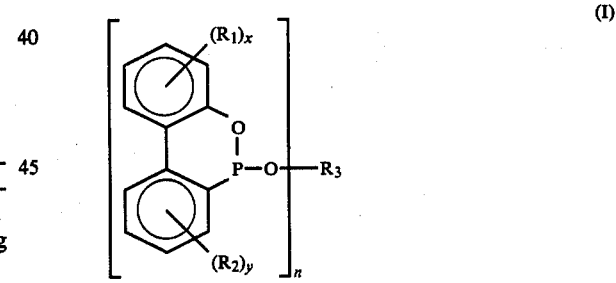

(I)

wherein
$R_1$ and $R_2$ independently of one another are a hydrocarbon radical, or halogen,
x and y independently of one another are 0, 1, 2 or 3,
n is 2, 3, 4, 5 or 6, and
$R_3$ is a n-valent aliphatic, alicyclic, aromatic, araliphatic each optionally containing N, O, or S atoms or heterocyclic hydrocarbon residue.

2. Phosphonites according to claim 1 of the formula I wherein
$R_1$ is $C_1$–$C_8$ alkyl,
x is 0, 1 or 2 and
y is 0,
n is 2, 3, 4, 5 or 6 and
$R_3$, if n is 2, denotes $C_2$–$C_{22}$ alkylene which may optionally be interrupted by —O—, —S— or —N($R_4$)—, whereby $R_4$ is $C_1$–$C_{18}$ alkyl, $C_5$–$C_{12}$ cycloalkyl, $C_6$–$C_{14}$ aryl, benzyl or allyl, and $R_3$ denotes furthermore butenylene or butynylene, $C_5$-$C_{12}$ cycloalkylene, $C_6$-$C_{14}$ arylene, $C_7$-$C_{22}$ alkarylene, 1,4-dithian-2,5-diyl or a residue of the formula —$CH_2$—$CH_2$—$R_5$—, wherein $R_5$ is a member of the group consisting of

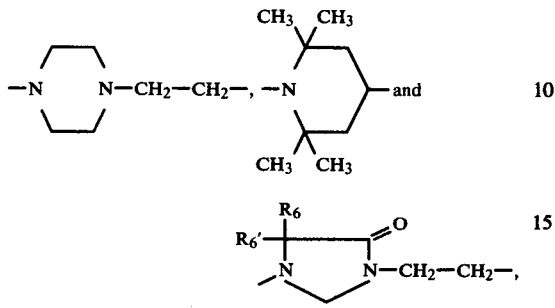

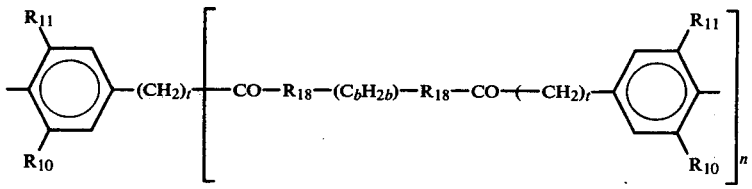

whereby $R_{13}$ denotes hydrogen or $C_1$-$C_8$ alkyl and
$R_{14}$ denotes hydrogen, $C_1$-$C_8$ alkyl or one of the groups —$(CH_2)_a$—$COOR_{15}$ or —$CH_2$—$CH(R_{16})$—$S$—$R_{17}$, wherein a is 1 or 2, $R_{15}$ denotes $C_1$-$C_{18}$ alkyl, $C_5$-$C_8$ cycloalkyl, phenyl or benzyl and $R_{16}$ is hydrogen or methyl and $R_{17}$ denotes $C_1$-$C_{18}$ alkyl, cyclohexyl, phenyl, benzyl or a group —$(CH_2)_a$—$COOR_{15}$ wherein a and $R_{15}$ are as defined above, or $R_{13}$ and $R_{14}$ together with the carbon atom to which they are attached form a ring containing 5 to 12 carbon atoms and $R_3$ denotes furthermore a group of the formula III

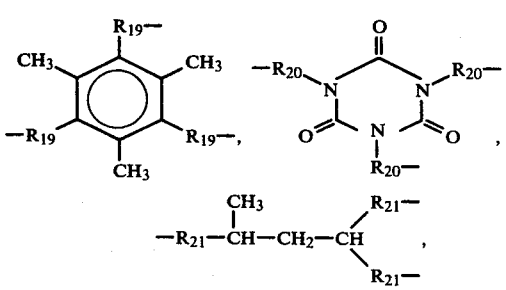

wherein $R_6$ and $R_6'$ denote independently of one another hydrogen or $C_1$-$C_6$ alkyl, and $R_3$ denotes furthermore a group of the formula

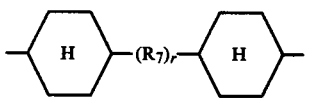

wherein r is 0 or 1 and $R_7$ denotes —O—, —S— or

whereby $R_8$ and $R_9$ denote independently of one another hydrogen or $C_1$-$C_8$ alkyl or $R_8$ and $R_9$ form together with the carbon atom to which they are attached a ring containing 5 to 12 carbon atoms, and $R_3$ denotes furthermore 1,4-cyclohexylenedimethylene; 1,3,3-trimethyl-cyclohexylene-1,5 or a group of the formula II

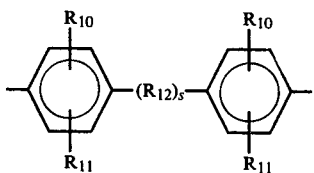

wherein s denotes 0 or 1, and
$R_{10}$ and $R_{11}$ denote independently of one another hydrogen, $C_1$-$C_{12}$ alkyl or cyclohexyl, and $R_{12}$ denotes —O—, —S— or wherein
t is 0, 1, 2 or 3
$R_{18}$ is —O— or —NH—,
b is 1 to 18, and
$R_{10}$ and $R_{11}$ are as defined above, and
n is 0 or 1 with the proviso that t cannot be 0 when n is 0, and
$R_3$, if n is 3, denotes a trivalent aliphatic $C_3H_5$ to $C_7H_{13}$ hydrocarbon radical or one of the groups

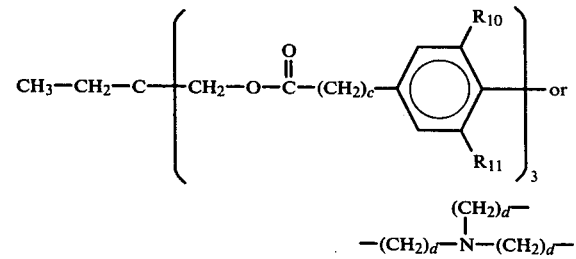

wherein d is 1 to 4 and
$R_{19}$ is a group of the formula IV

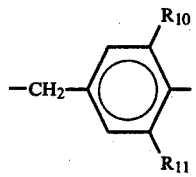

and $R_{10}$ and $R_{11}$ are as defined above, and $R_{20}$ is a group of the formula IV wherein $R_{10}$ and $R_{11}$ are as defined above, or $R_{20}$ is —CH$_2$—CH$_2$— or a group of the formula V

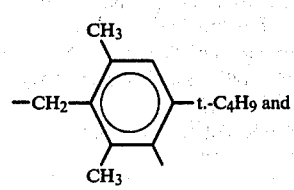

$R_{21}$ denotes a group of the formula VI

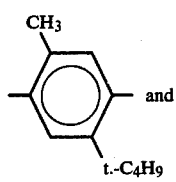

c is 0, 1, 2 or 3, and
$R_3$, if n is 4, denotes a tetravalent aliphatic $C_4H_6$ to $C_{10}H_{18}$ hydrocarbon radical or one of the groups VII or VIII

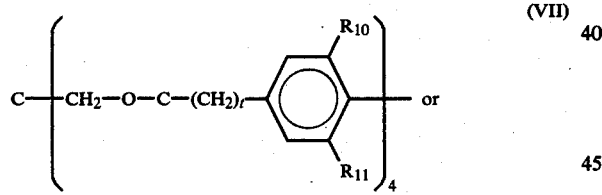

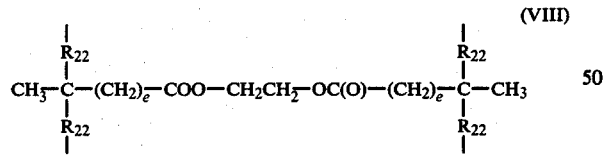

wherein $R_{22}$ is a group of the formula VI and e denotes 1 or 2, and t is as defined above, and
$R_3$, if n is 5, denotes a pentavalent aliphatic $C_5H_7$ to $C_{10}H_{17}$ hydrocarbon radical or the group IX

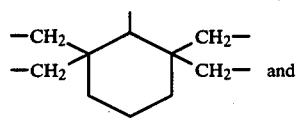

$R_3$, if n is 6, denotes a hexavalent aliphatic $C_6H_8$ to $C_{10}H_{16}$ hydrocarbon radical.

3. Phosphonites according to claim 2 of the formula I wherein
x and y are 0, and
n is 2, 3 or 4, and
$R_3$, if n is 2, denotes $C_2$-$C_9$ alkylene which may optionally be interrupted by —O— or —S—, or $R_3$ denotes furthermore phenylene, or phenylene, which is mono- or dialkylated with a total number of 7 to 22 carbon atoms or a group of the formula II*

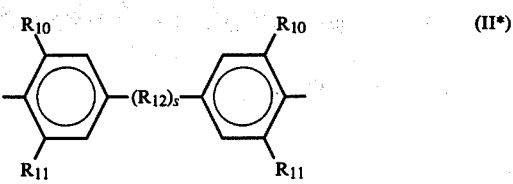

wherein
S denotes 0 or 1, and
$R_{10}$ and $R_{11}$ denote independently of one another hydrogen or $C_1$-$C_8$ alkyl and $R_{12}$ denotes —O—, —S— or

whereby
$R_{13}$ is hydrogen or methyl, and
$R_{14}$ is hydrogen, methyl or one of the groups $(CH_2)_a$—COR$_{15}$ or —CH$_2$—CH(R$_{16}$)—S—R$_{17}$ wherein a and $R_{16}$ are as defined above and $R_{15}$ denotes $C_1$-$C_{18}$ alkyl and $R_{17}$ is $C_1$-$C_{12}$ alkyl or a group of the formula —(CH$_2$)$_a$—COOR$_{15}$, wherein a and $R_{15}$ are as herein defined and $R_3$ denotes furthermore a group of the formula III wherein $R_{10}$ denotes methyl or t.butyl and $R_{11}$ is t.butyl, $R_{18}$ is —O— or —NH—, t is 2, b is 5 to 6 and n is 1, and $R_3$ if n is 3, denotes a trivalent aliphatic $C_3H_5$ to $C_7H_{13}$ hydrocarbon radical or a group of the formula

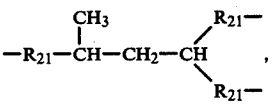

wherein
$R_{21}$ is as defined in claim 2, and
$R_3$ if n is 4, denotes a group of the formula VII, wherein t is 2 and $R_{10}$ and $R_{11}$ denote t.butyl.

4. Phosphonites according to claim 3 of the formula I wherein
x and y are 0, and
n is 2 or 3, and
$R_3$ if n is 2, denotes $C_2$-$C_6$ alkylene, which may be optionally interrupted by —O— or —S—, or $R_3$ denotes phenylene, phenylene, which is mono- or di-alkylated with total number of carbon atoms of 7-22, or a group of the formula II* wherein s denotes 0 or 1, and $R_{10}$ and $R_{11}$ denote independently of one another hydrogen, methyl, t.butyl, t-pentyl or 1,1,3,3-tetramethylbutyl and $R_{12}$ is —O—, —S— or

wherein $R_{13}$ and $R_{14}$ are hydrogen or methyl, and $R_3$ denotes furthermore a group of the formula III wherein $R_{10}$ denotes methyl or t.butyl and $R_{11}$ denotes t.butyl, $R_{18}$ is —O—, t is 2, b is 2 to 6 and n is 1, and $R_3$, if n is 3, denotes

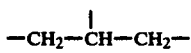

or a group of the formula

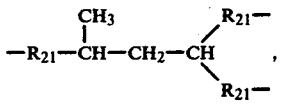

wherein
$R_{21}$ is as defined in claim 3.

5. Phosphonites according to claim 1, of the formula I, wherein n is 2 or 3.

6. Phosphonites according to claim 2, wherein n is 2, and $R_3$ denotes $C_7$–$C_{22}$ alkarylene, or a group of the formula II.

7. A composition stabilized against oxygen, light and heat comprising an organic material containing from 0.005 to 5% of a phosphonite according to claim 1.

8. A composition according to claim 7 wherein said organic material is a polyolefin.

9. The composition according to claim 8 wherein said polyolefin is polypropylene.

* * * * *